United States Patent [19]
Conway et al.

[11] Patent Number: 5,102,405
[45] Date of Patent: * Apr. 7, 1992

[54] CONTRACEPTIVE HOOD

[75] Inventors: Anthony J. Conway; Peter R. Conway, both of Chatfield; Philip J. Conway, Stewartville, all of Minn.

[73] Assignee: Carter-Wallace, Inc., New York, N.Y.

[*] Notice: The portion of the term of this patent subsequent to Apr. 17, 2007 has been disclaimed.

[21] Appl. No.: 563,791

[22] Filed: Aug. 3, 1990

Related U.S. Application Data

[63] Continuation of Ser. No. 50,579, May 13, 1987, abandoned, which is a continuation of Ser. No. 6,986, Jan. 26, 1987, Pat. No. 4,917,113, which is a continuation of Ser. No. 715,608, Mar. 25, 1985, Pat. No. 4,638,790, which is a continuation-in-part of Ser. No. 577,602, Feb. 10, 1984, abandoned, which is a continuation-in-part of Ser. No. 475,852, Mar. 16, 1983, abandoned.

[51] Int. Cl.$^5$ .............................................. A61F 5/44
[52] U.S. Cl. ..................................... 604/352; 128/844
[58] Field of Search ........................... 128/842, 844; 604/349–353

[56] References Cited

U.S. PATENT DOCUMENTS

| | | | |
|---|---|---|---|
| 4,475,910 | 10/1984 | Conway et al. | 604/352 |
| 4,638,790 | 1/1987 | Conway et al. | 604/352 |
| 4,917,113 | 4/1990 | Conway et al. | 128/844 |

OTHER PUBLICATIONS

"Prophylactic", Webster's New Collegiate Dictionary G&C Merriam Co.

Primary Examiner—Randy C. Shay
Attorney, Agent, or Firm—Kinney & Lange

[57] ABSTRACT

A male contraceptive hood which is adhesively secured to the penis, the hood being initially rolled up and the interior of the hood being free of adhesive until it is unrolled. The hood has a thin sheath which serves as the contraceptive device and an outer cylindrical member which is initially rolled together with the thin sheath. The outer cylindrical member has an adhesive on a portion of its outer surface, separated from the outer surface by a release agent, the adhesive being transferred to the inner surface of the sheath as the hood is unrolled onto a penis. The outer member can then be removed leaving only the thin inner sheath on the penis. A projecting portion is provided on the outer member for grasping the outer member to remove it.

In a preferred form, a lubricant is disposed between the sheath and the inner surface of the outer cylindrical member. This lubricant remains on the outer surface of the sheath to facilitate removal of the outer member and also to aid in intercourse.

The contraceptive hood may be either relatively short so as to extend only slightly beyond the head of the penis, or sufficiently long to extend over substantially the entire length of the penile shaft.

6 Claims, 5 Drawing Sheets

Fig. 3
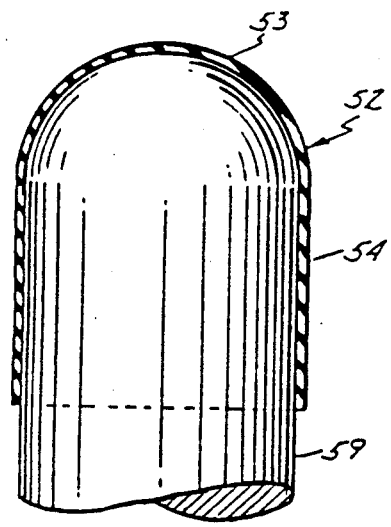
Fig. 4
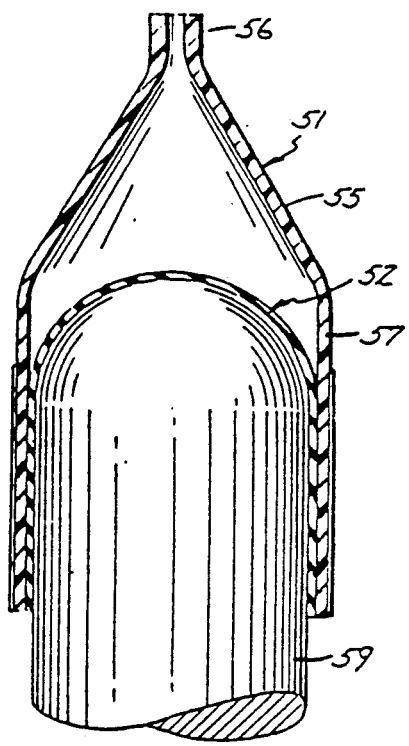
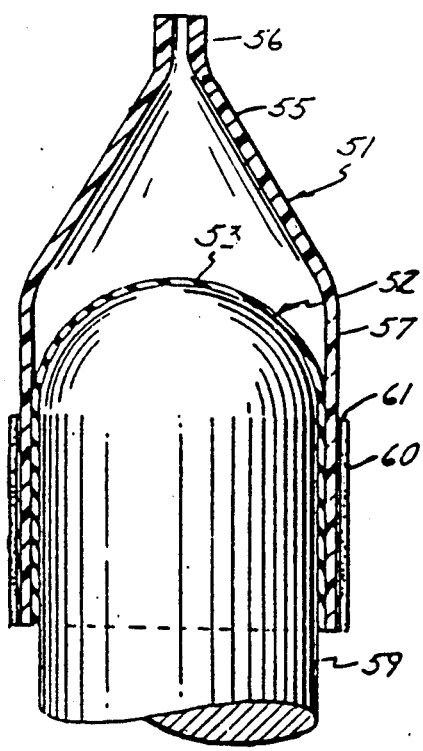
Fig. 5
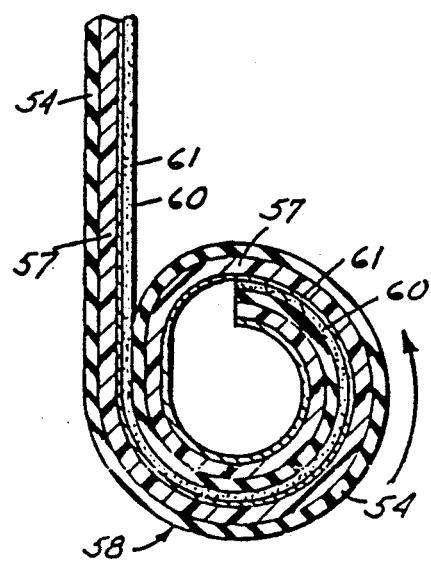
Fig. 6

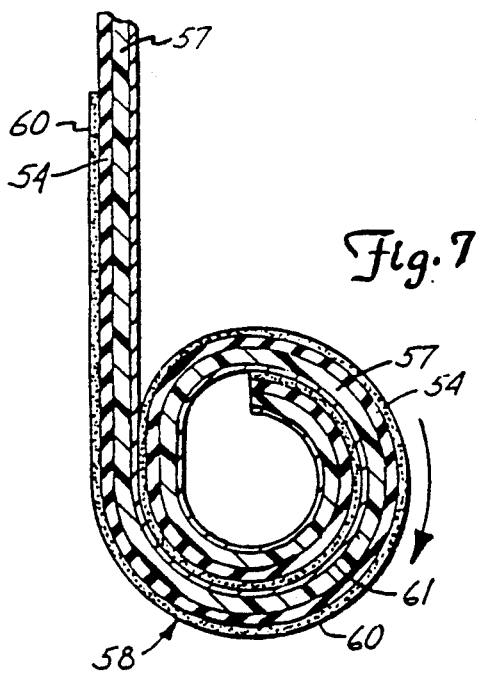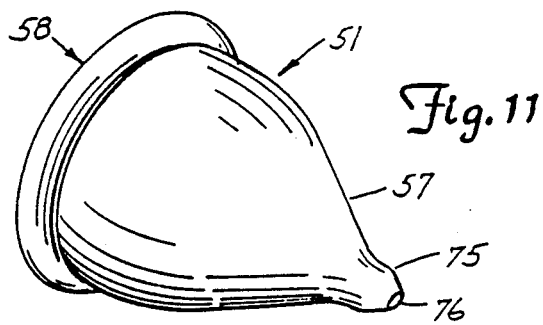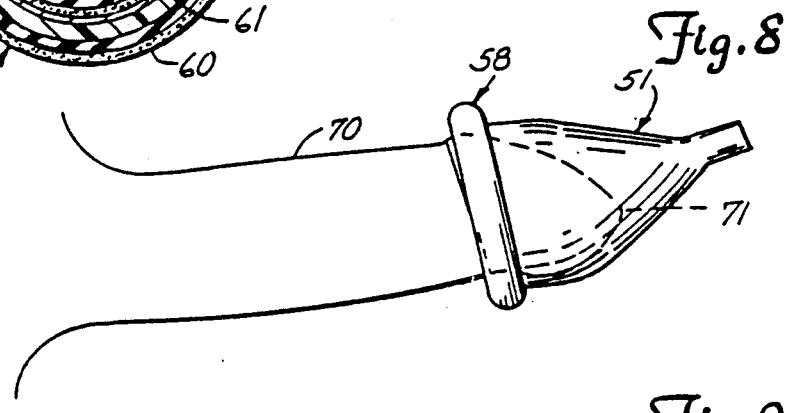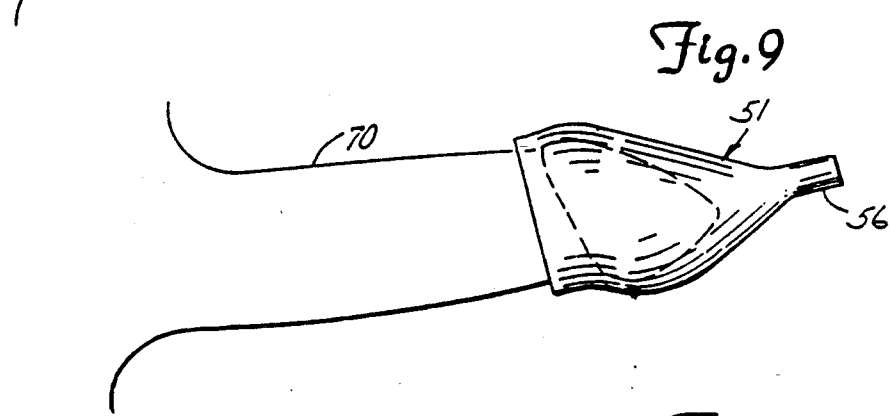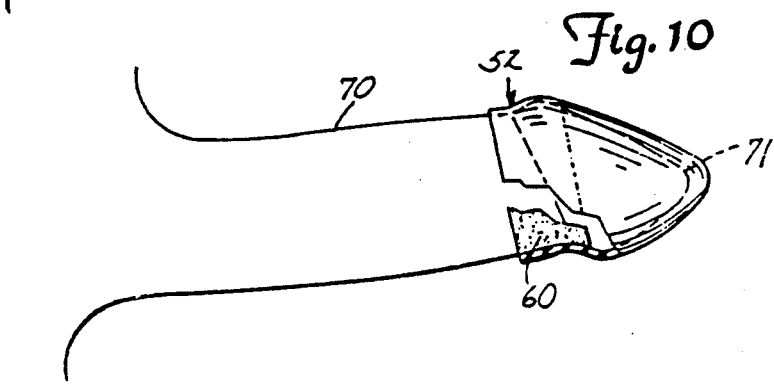

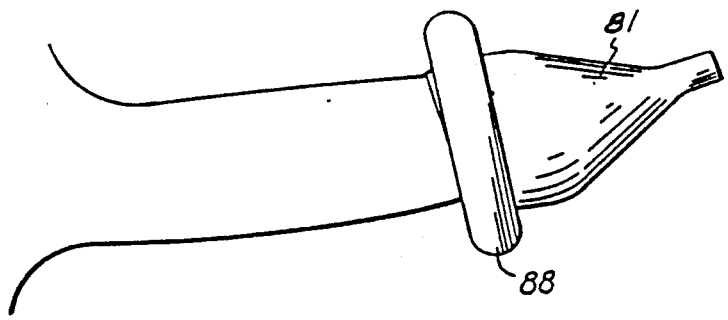
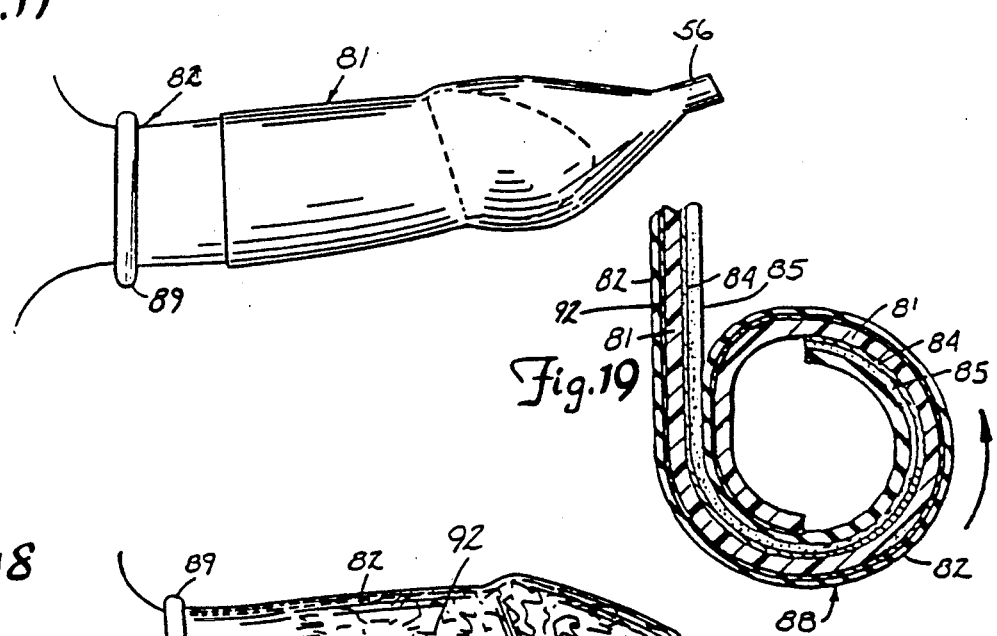
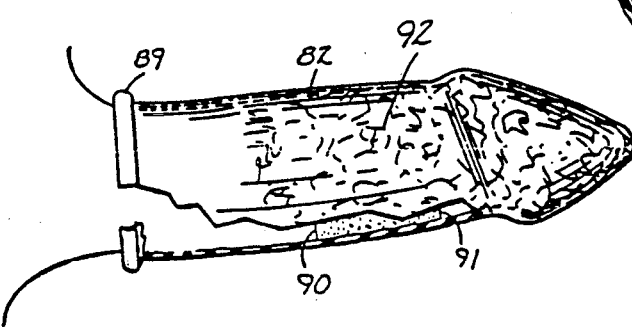

CONTRACEPTIVE HOOD

This is a continuation of application Ser. No. 07/006,986, filed Jan. 16, 1987, now U.S. Pat. No. which is a continuation of application Ser. No. 06/715,608, filed Mar. 25, 1985, now U.S. Pat. No. 4,638,790, which is a continuation-in-part of application Ser. No. 577,602, filed Feb. 10, 1984, now abandoned, which in turn is a continuation-in-part of earlier application Ser. No. 475,852, filed Mar. 6, 1983, now abandoned.

BACKGROUND OF THE INVENTION

1. Field of the Invention

The present invention relates to male contraceptive hoods which are adhesively secured to the penis, the hood being initially rolled up with an outer thicker member, and the interior of the hood being free of adhesive until it is unrolled.

2. Description of the Prior Art.

The conventional contraceptive condom is designed to cover not only the penile head but the entire penile shaft. It is usually used initially in a rolled up condition and is unrolled to extend for substantially the full length of the penile shaft. It is retained in position largely by friction between the inner wall of the condom and the penis. An objection to condoms of this type is that they tend to slip off the penis after ejaculation has occurred and the penis tends to assume a flaccid condition. This may result in semen accidentally entering the vaginal passage.

Recognizing the drawback of the conventional condom, various attempts have been made to provide a contraceptive hood which is adhesively secured to the penis. The early United States Woodruff patent, U.S. Pat. No. 822,092, for example, shows a short contraceptive hood in which there is adhesive applied to the interior. It is obviously very difficult to apply such a contraceptive hood when adhesive is already in place. Furthermore, the arrangement of the Woodruff patent has the drawback that it provides a long extending nipple which would interfere with the sexual act. The United States Patents to Kopelowicz, U.S. Pat. No. 3,951,141; Wayne, U.S. Pat. No. 2,448,938; and Czirely, U.S. Pat. No. 3,677,225 all show arrangements in which there is an adhesive over a portion of the interior of a short contraceptive hood with a release strip of some kind which is stripped off in connection with applying the contraceptive hood to the penis. The arrangements of these patents all have the drawback, however, a separate release strip is necessary and that the adhesive is not always located where it is most effective. The Ormo U.S. Pat. No. 2,839,060 shows an arrangement in which adhesive is applied on the inner surface of an inner sheath. There is also a ridge that acts as a sealing device. The device can be relatively complicated to apply partly due to the continual presence of the adhesive on the inner surface. The Warner U.S. Pat. No. 3,648,700 shows a contraceptive device in which there are bands which are used for overlapping encirclement of the penis behind the tip, these overlapping bands being coated on the inside with adhesive. Such an arrangement provides an adhesive over only a very limited area of the contraceptive hood and further provides a very irregular surface due to the space between the strap and the main portion of the hood and also due to a thickened portion resulting from the overlapping portions of the straps. The Welsh U.S. Pat. No. 2,389,831 shows a protective covering for a member of the body, such as finger or toe. Initially, there is adhesive on an outer surface. This is covered by a protective tape which must be removed. In order to bring the adhesive into the inner surface, the entire unit is turned inside out. This would be very difficult to manipulate as a contraceptive device.

In our prior U.S. Pat. No. 4,475,910, we disclosed an arrangement in connection with a condom catheter for transferring adhesive from the outer surface of the catheter to the inner surface as it is rolled and unrolled. This arrangement, if applied to a contraceptive hood, would not be satisfactory for several reasons. In the first place, it employs a release layer which is left on the outer surface of the sheath when unrolled. While this is entirely satisfactory in connection with a catheter, it would be unsatisfactory in connection with a condom because of the fact that the release layer would be present on the outer surface during intercourse and would tend to rub off. Furthermore, it becomes very difficult to use an arrangement such as this where a relatively short contraceptive hood is being used. These are customarily rolled up prior to being applied to the penis, and in the case of a relatively short contraceptive hood, which is always of relatively thin material, the roll becomes so small in size as to make it difficult to unroll.

SUMMARY OF THE INVENTION

The present invention is concerned with a contraceptive hood of the type in which there is a second outer member, on the outer surface of which there is an adhesive, release agent so that when the inner and outer members are rolled together the adhesive adheres only to the inner surface of the sheath. The inner and outer members are rolled up together with the adhesive adherring to the inner surface of the thin inner cylindrical member as the unit is unrolled.

The hood may be relatively short so as to cover only the head of the penis or may be sufficiently long to cover the entire penile shaft.

The outer thick portion is removed after the contraceptive hood is in place. This can be readily accomplished since the adhesive has been transferred to the inner surface of the inner thin portion. The release agent is still on the thick portion and is removed when the thick portion is removed. The outer thick portion may be provided with a projecting portion which may be grasped to pull it loose from the inner thin portion. To facilitate withdrawal of the outer portion, the outer thick portion is provided with a small aperture to permit air to enter between the inner thin member and the outer thick member as the latter is withdrawn so as to prevent a vacuum being formed in the outer portion is withdrawn. To further facilitate withdrawal of the outer portion, a lubricant is applied between the inner and outer portions. This lubricant not only facilitates withdrawal of the outer portion but also remains on the outer surface of the thin inner sheath to facilitate its use during intercourse. This lubricant is preferably applied to the inner surface of the outer member and is transferred to the outer surface of the thin inner member when the two portions are rolled together.

The adhesive layer is preferably applied over that portion of the length of the hood adjacent the open end which is engaged by the inner surface of the cylindrical member when the cylindrical member is in rolled up condition.

BRIEF DESCRIPTION OF THE DRAWINGS

FIG. 3 is a view of the thin inner member of the contraceptive hood of FIGS. 1 and 2 placed over a mandrel;

FIG. 4 is a view showing the thick outer portion of the cylindrical member which has been applied to the thin inner portion while still on the mandrel;

FIG. 5 is similar to FIG. 4, showing a release layer and an adhesive layer which have been applied to the outer surface of the thicker outer portion;

FIG. 6 is a view on a highly enlarged scale of a portion of the contraceptive hood of FIGS. 1 and 2 which is shown as being rolled up to show the various layers of the hood;

FIG. 7 is a view similar to FIG. 6 but showing the hood being unrolled to show the transfer of adhesive from the outer surface of the outer member to the inner surface of the inner member:

FIG. 8 is a view showing the contraceptive hood of FIGS. 1 and 2 being applied to the tip of a penis, the device still being partially rolled up;

FIG. 9 is a view similar to FIG. 8 but with the contraceptive hood unrolled on the tip of a penis;

FIG. 10 is a view showing the hood after the outer cylindrical member has been removed;

FIG. 11 is a perspective view of a modification of the outer member as far as means for removing the outer cylindrical member is concerned;

FIGS. 16 through 19 are views, similar to FIGS. 12 through 15, of a further modification of the invention.

DETAILED DESCRIPTION OF THE PREFERRED EMBODIMENTS

Figure 1:
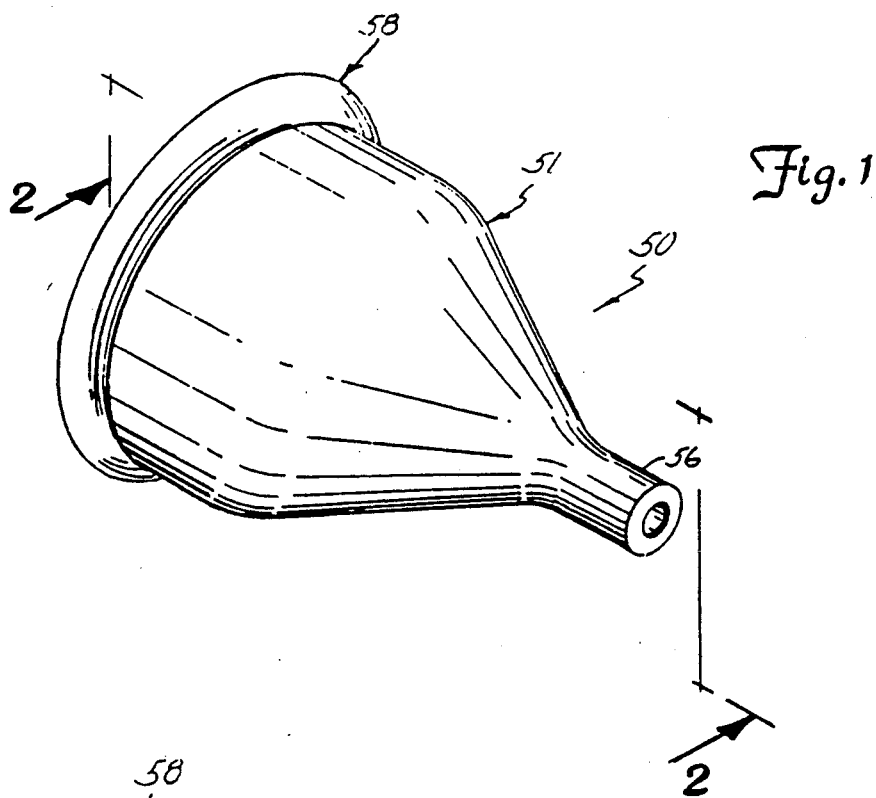
FIG. 1 is a perspective view of one form of our contraceptive hood prior to the same being applied to a penis.
Figure 2:
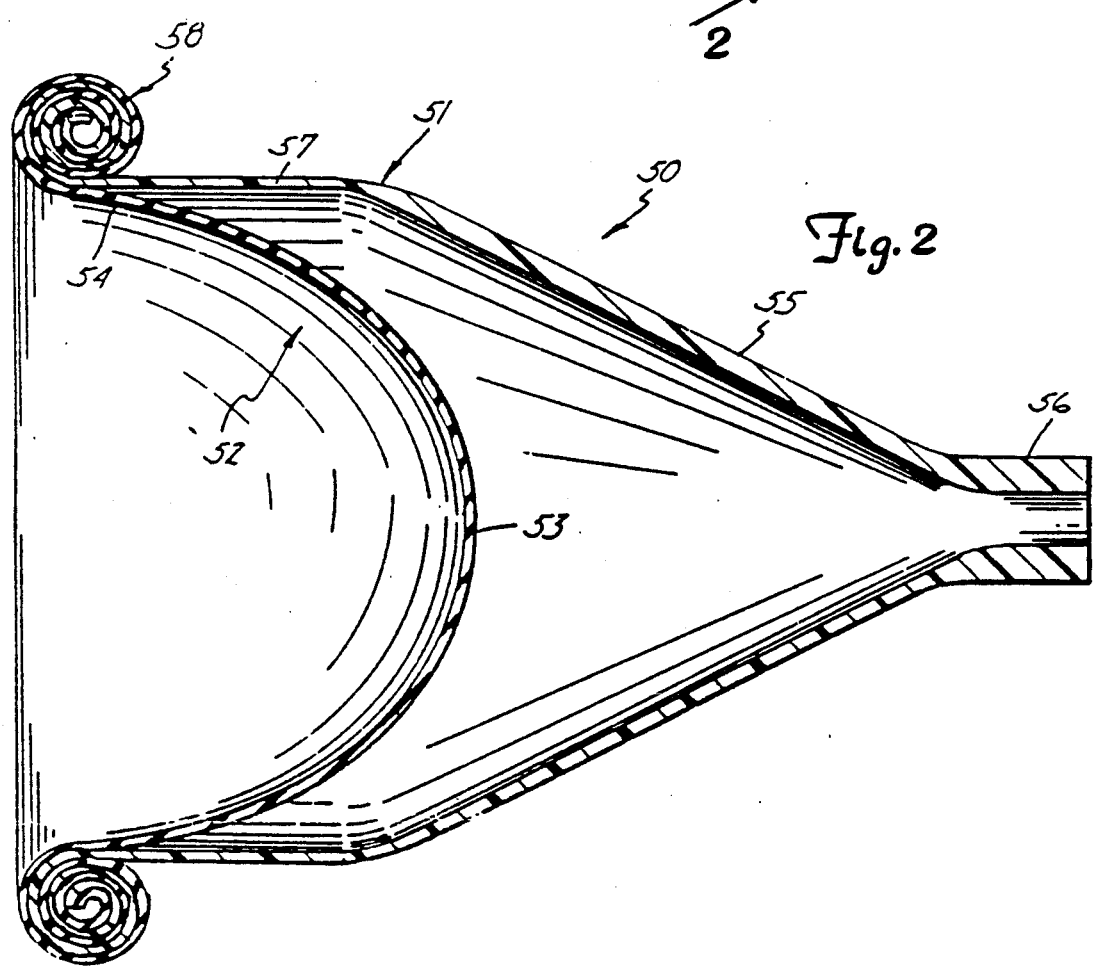
FIG. 2 is a sectional view of the contraceptive hood, the section being taken along the line 2—2 of FIG. 1.

Referring specifically to FIGS. 1 and 2, the two-piece hood is generally designated by the reference numeral 50. There is an outer portion 51 and an inner portion 52 which is made of very thin resilient material having a thickness of between .002 and 0.004 inches. It has a bowl portion 53 and a major sheath portion 54.

The outer portion 51 has a conical portion 55 which terminates in a projecting tubular portion 56. This projecting portion 56, as will be pointed out later, can take various forms so long as it provides a means for grasping the outer member 51 when it is desired to remove it, as will be explained later.

The outer member 51 is made of relatively thick material which may be from 0.015 to 0.025 inches in thickness and has a body portion 57 which is rolled with the sheath portion 54 to form a roll 58.

As will be explained in more detail later, the outer portion of the cylindrical member 51 is coated with a release layer and an adhesive so that adhesive is transferred in the roll 58 to the inner surface of member 52. After the condom hood is unrolled, the outer member 51 can be pulled loose by grasping the projection 56. It can then be discarded, leaving only the inner member 52 on the penis. The release agent remains on the outer member 51.

FIGS. 3, 4 and 5 are directed to a method of forming the two part condom hood of FIGS. 1 and 2.

Referring first to FIG. 3, it will be noted that the inner member 52 has been placed upon a mandrel 59 which has a curved upper end corresponding to the curvature of the dome shape portion 53 of the inner member 52.

Referring now to FIG. 4, the outer member 51 of the hood has been placed over the inner member 52, the lower ends of both the outer portion 51 and the inner portion 52 terminating at the same point on the mandrel 59.

In FIG. 5, there has been applied to the outer surface of the body portion 57 of the outer member 51 an adhesive release layer 61, which may, for example, be any conventional silicone release agent, and a layer of pressure sensitive adhesive 60.

The unit is now rolled up by rolling up the various layers together starting at the lower end. A portion of the sheath in a highly enlarged scale is shown in FIG. 6 with the layers in the position they assume as the sheath is rolled up. It will be noted that the release layer 61 and adhesive layer 60 are still on the body portion 57 of the outer member 51. The various layers are rolled together to form a roll 58 and when the rolling is completed, the device will appear as shown in FIGS. 1 and 2.

FIG. 7 is a view similar to FIG. 6 but showing the elements as the sheath is being unrolled in its application to a penis. It will be noted that the adhesive layer 60 is now on the inner surface of the sheath 54 of the inner member 52. This has taken place because of the fact that the adhesive layer 60 comes adjacent the inner surface of sheath 54 when the device is in the rolled up position of FIGS. 2 and 7. Because of the release layer 61, the adhesive adheres to the inner surface of the sheath 54 rather than to the outer surface of the outer member 57. Thus, the adhesive is transferred from the outer surface of the outer member to the inner surface of the sheath.

In FIGS. 8 through 10, we have shown the method by which the condom hood of FIGS. 1 and 2 is placed on the penis. As shown in FIG. 8, the inner and outer sheath, still rolled together in a roll 58, are placed over the tip 71 of the penis 70.

In FIG. 9, we have shown the condom hood as having been unrolled. It will be noted that the unrolled sheath extends over only a short portion of the penile shaft beyond the shaft to have the major portion of the penile shaft bare to increase the sensitivity of the penis during the intercourse. Because of the fact that the adhesive has been transferred from the outer surface of member 51 to the inner surface of the member 52, it is possible to grasp the projecting portion 56 of the outer member 51 and pull it loose. It can now be pulled off and discarded. Since the release agent has remained on the outer surface of the outer member, it is withdrawn along with the outer member. After the outer member 51 has been pulled off, the device assumes the appearance of FIG. 10. It will be noted that the adhesive 60 extends over a band beginning at the open end of the inner hood member 52 to a point overlapping the head of the penis. This will be effective to retain the hood in place even though it extends over only the outer portion of the penis.

In FIG. 11, I have shown a slight modification of the species of FIGS. 1 through 10. For purposes of ready comparison, similar reference characters have been used for corresponding elements. The only difference between the arrangement of FIG. 11 and that of FIGS. 1 through 10 is that instead of there being a tubular projection 56, there is a nipple type of projection 75. This nipple type of projection has an aperture 76 through it. The purpose of the aperture 76 is to provide a means for admitting air between the inner and outer members as the outer member 51 is withdrawn. Otherwise, there would be a tendency for a suction to be created. In the arrangement shown in FIGS. 1 through 9, this is provided for because the projection 56 is tubular and the air can be freely admitted between the inner and outer members. Where, however, a nipple 75 is employed for grasping the outer member 51 when it is desired to remove it, it is desirable to have a passage such as opening 76 to admit the air. While the device can function without such a passage, it does facilitate the removal of the outer member 51.

MODIFICATION OF FIGS. 12-14

Figure 12:
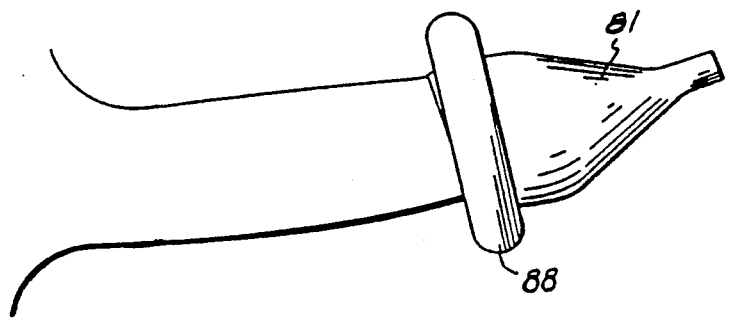
FIG. 12 is a view of a further modification of our invention in which there is a two-part hood as in FIGS. 1-10, but in which the condom hood covers substantially the entire penile shaft, the device being shown in FIG. 12 as being initially applied to the penis.
Figure 13:
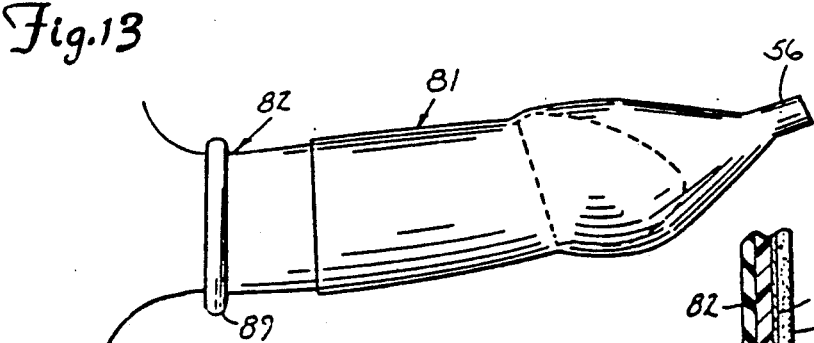
FIG. 13 is a view of the same hood with the outer member completely unrolled and the inner member unrolled to the base of the penis.
Figure 14:
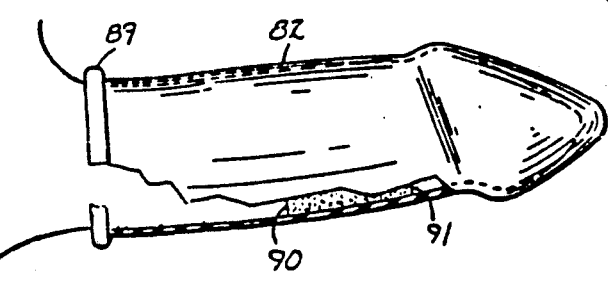
FIG. 14 is a view in which the outer member has been pulled away from the inner member.

The modification of FIGS. 12-14 is the same as that of FIGS. 1-11, except for the fact that the contraceptive hood is longer to extend over the full length of the penile shaft. While the outer member is longer than that of FIGS. 1-11, it is shorter than the inner member so that the outer member will be fully unrolled before the inner member reaches the base of the penile shaft.

Figure 15:
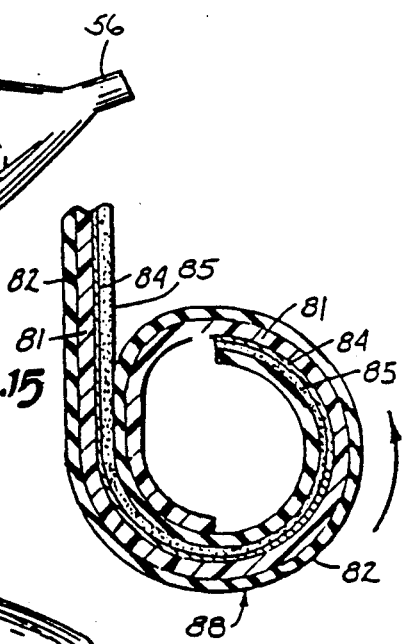
FIG. 15 is a sectional view on a large scale showing a portion of the contraceptive hood of FIGS. 16-17 being rolled up and showing the various layers of the hood.

Referring to FIGS. 12 and 13, the outer member is indicated by the reference numeral 81 and the inner member is indicated by the reference numeral 82. Initially, as shown in FIG. 15, the outer member has a layer of adhesive 85 with a release layer 84 between the adhesive and the outer surface of the outer member 81. As best shown in FIG. 13, in which the members have been unrolled, the outer member 81 in this modification is substantially shorter than the inner member 82. As in the previous species, it is thicker than the inner member. The relative thicknesses of the inner and outer members are substantially the same as in the species of FIGS. 1-11. The outer member, similar to member 51, has a conical outer portion S5 and an extending tubular portion 56 which acts as a means for withdrawal of the outer member 81 when it is in the unrolled condition shown in FIG. 13. Initially, the inner and outer members are rolled together, as in the preceding species, to form a roll 88. In FIG. 15, there is a sectional view of the roll 88 with the members being shown in the process of being rolled up. It will be noted that the inner end of the outer member 81 does not extend as far into the roll as the outer member 82.

In use, the contraceptive hood is applied to the tip of the penis in the same manner as in the other species. This is shown in FIG. 12. The contraceptive hood is then unrolled. Initially, the outer member 81 will be completely unrolled. The user then continues to unroll the inner member 82, normally leaving a small roll 89 at the base of the penis.

In the process of rolling and unrolling, the adhesive 85 is transferred from the outer surface of the outer member 81 to the inner surface of member 82 just as in the species of FIGS. 1-11. The primary difference, however, is that the layer of adhesive 90, shown in the broken away portion of FIG. 14, extends much further than the layer of adhesive in the species of FIGS. 1-11, and as shown in FIG. 10. In one particular instance, an adhesive layer of one and one-half inches was used. This started just back of the tip of the penis. In a typical case, the outer member 81 was about four inches long.

It will be obvious that the operation, except for the difference in length of the inner and outer members, is basically the same as in the species of FIGS. 1-11. When the unit has been unrolled to the position shown in FIG. 13, the adhesive originally on the outer surface of member 81 has been transferred to the inner surface of the inner member 82. All that remains on the outer member is some of the adhesive release material. This is drawn off with the outer member. Thus, the outside of the inner sheath S1 is free of any release material or adhesive.

Because of the presence of the adhesive 90 over a substantial portion of the sheath, the sheath is held in place even after ejaculation has occurred. In this way, the contraceptive hood of this invention is much safer to use than the conventional type of hood which tends to become loose on the penis after ejaculation has occurred.

MODIFICATION OF FIGS. 16 THROUGH 19

The modification of FIGS. 16 through 19 is very similar to that of FIGS. 12 through 15, with one very important exception. A lubricant such as a medical silicone lubricant is applied to the interior of the outer member 81 prior to the outer member and the inner sheath being rolled together. This lubricant is transferred, in the rolled up condition, to the outer wall of the inner sheath 82. Referring to FIG. 19, the layer of lubricant is indicated by reference numeral 92. It will be noted that this lubricating layer 92 is between the outer sheath 81 and the inner sheath S2. When in the rolled up condition shown in FIG. 19, the lubricant will obviously adhere to the outer surface of the inner sheath 82. The lubricant has two functions. In the first place, it makes it very easy to withdraw the outer member 81, since the entire area of the inner sheath 82 over which the outer member extends is lubricated. In the second place, the layer of lubricant 92 which extends, after the outer member has been removed, over the area covered by the outer member 81, as shown in FIG. 1, acts as a lubricant for intercourse. In other words, the condom becomes a prelubricated condom.

CONCLUSION

In conclusion, it will be seen that we have provided a contraceptive hood which is initially rolled with an outer cylinder member, there being a pressure sensitive adhesive layer between the hood and the outer member. As the hood is unrolled onto the penis, the adhesive surface adheres only to an inner surface of the contraceptive hood to cause the hood to firmly adhere to the penis. After the contraceptive hood has been unrolled onto the penis, the outer member is then withdrawn. The withdrawal may be facilitated by providing a lubricating layer between the inner and outer cylindrical members, This lubricating layer remains on the inner member after the outer member has been withdrawn to provide lubrication during intercourse.

What is claimed is:

1. A contraceptive hood to be adhesively applied to an erect penis, said contraceptive hood including:
   a flexible cylindrical member generally conformable to the head of the penis having a closed end and an open end;
   said cylindrical member being rolled outwardly upon itself onto the penis from said open end; and
   an adhesive layer and an adhesive release layer disposed between the rolls and the adhesive release layer disposed between said adhesive layer and the outer surface of said cylindrical member so that upon said member being unrolled onto the head of an erect penis, the adhesive layer releases from the adhesive release layer due to the unrolling of the cylindrical member and adheres to the inner surface of said cylindrical member to cause the cylindrical ember to adhere to the erect penis.

2. The contraceptive hood of claim 1 in which the hood is of a length comparable to the head of a typical penis.

3. The contraceptive hood of claim 1 in which the hood is of a length comparable to the length of the penile shaft of a typical penis.

4. The contraceptive hood of claim 1 in which the cylindrical member is a thin member and in which the adhesive layer and the release layer are applied directly to the outer wall of said thin cylindrical member.

5. The contraceptive hood of claim 1 in which the layer of adhesive which extends over only that portion adjacent the open end which is engaged by the inner surface of the cylindrical member when said cylindrical member is in rolled up condition.

6. The method of applying a contraceptive hood to the head of a penis while leaving the penis shaft uncovered, said method comprising:
   unrolling onto a penis an initially rolled up, closed end, condom type hood having, pressure sensitive adhesive and an adhesive release layer disposed between the rolls, said adhesive releasing from the adhesive release layer due to the unrolling of the cylindrical member and attaching to the inner surface of the hood as said hood is unrolled;
   continuing said unrolling until the head of the penis is covered and stopping before the hood extends over any major portion of the penile shaft; and
   pressing the hood firmly against and around the penis to cause the hood to adhere securely to the area adjacent the head of the penis.

* * * * *